United States Patent
Bindra et al.

(10) Patent No.: US 12,361,383 B2
(45) Date of Patent: Jul. 15, 2025

(54) METHODS AND SYSTEMS FOR BI-DIRECTIONAL INTEGRATION BETWEEN AN INTRAORAL SCANNER AND A DENTAL LAB

(71) Applicant: TechCo Holdings, Inc., Wilmington, DE (US)

(72) Inventors: Harmeetpal Singh Bindra, Gurgaon (IN); Niranjan Ramakrishnan, Tamil Nadu (IN)

(73) Assignee: TECHCO HOLDINGS, INC., Wilmington, DE (US)

( * ) Notice: Subject to any disclaimer, the term of this patent is extended or adjusted under 35 U.S.C. 154(b) by 179 days.

(21) Appl. No.: 18/189,825

(22) Filed: Mar. 24, 2023

(65) Prior Publication Data
US 2023/0307108 A1    Sep. 28, 2023

Related U.S. Application Data

(60) Provisional application No. 63/341,247, filed on May 12, 2022, provisional application No. 63/341,248, (Continued)

(30) Foreign Application Priority Data

Mar. 25, 2022  (IN) .............................. 202241017085
Mar. 25, 2022  (IN) .............................. 202241017090
Mar. 25, 2022  (IN) .............................. 202241017136

(51) Int. Cl.
*G06Q 10/10*    (2023.01)
*A61B 5/00*    (2006.01)
(Continued)

(52) U.S. Cl.
CPC ......... *G06Q 10/103* (2013.01); *A61B 5/0013* (2013.01); *G06Q 10/06395* (2013.01);
(Continued)

(58) Field of Classification Search
None
See application file for complete search history.

(56) References Cited

U.S. PATENT DOCUMENTS 10,299,891 B2    5/2019  Lemchen et al.
10,509,838 B2 *  12/2019 Elbaz ..................... A61C 1/088
(Continued)

FOREIGN PATENT DOCUMENTS

WO    WO-2021046434 A1 *  3/2021    ......... A61C 13/0004

OTHER PUBLICATIONS

Brownrigg, Danae Cassandra. "The Effect of Root and Bone Visualization on Perceptions of the Quality of Orthodontic Treatment Simulations." Order No. 10142069 University of Minnesota, 2016. Ann Arbor: ProQuest. Web. Feb. 28, 2025. (Year: 2016).*

*Primary Examiner* — Lena Najarian
(74) *Attorney, Agent, or Firm* — HSML P.C.

(57) ABSTRACT

Methods and systems for bi-directional integration between one or more intraoral scanners and one or more dental labs are provided. A dental product management platform connecting the one or more intraoral scanners and the one or more dental labs can: receive an instruction to create a new dental product prescription from an operator via a graphical user interface (GUI) of the dental product management platform provided on a particular intraoral scanner, receive scanned image data from the particular intraoral scanner; validate the scanned image data in real time to determine whether the scan is of acceptable quality to fabricate a dental product; and upon determining that the scanned image data is not of acceptable quality, provide a notification to the operator via the GUI to use the particular intraoral scanner to take a second scan of the patient using the particular intraoral scanner.

8 Claims, 7 Drawing Sheets

Related U.S. Application Data filed on May 12, 2022, provisional application No. 63/341,251, filed on May 12, 2022.

(51) Int. Cl.
  *G06Q 10/0639* (2023.01)
  *G06Q 10/087* (2023.01)
  *G06Q 40/06* (2012.01)
  *G16H 20/10* (2018.01)
  *G16H 30/20* (2018.01)

(52) U.S. Cl.
  CPC ........... *G06Q 10/087* (2013.01); *G06Q 40/06* (2013.01); *G16H 20/10* (2018.01); *G16H 30/20* (2018.01)

(56) References Cited

U.S. PATENT DOCUMENTS

| | | | |
|---|---|---|---|
| 10,548,691 B2 | 2/2020 | Lemchen et al. | |
| 10,595,966 B2 * | 3/2020 | Carrier, Jr. | G06V 20/50 |
| 11,284,969 B2 | 3/2022 | Lemchen et al. | |
| 2014/0249839 A1 * | 9/2014 | Rickard | G16H 10/40 |
| | | | 705/2 |
| 2016/0259515 A1 * | 9/2016 | Sabina | G06F 3/04883 |
| 2021/0321872 A1 * | 10/2021 | Saphier | G06V 20/64 |
| 2022/0233284 A1 * | 7/2022 | Fridman | G16H 40/67 |

* cited by examiner

Fig. 3

AI Scan Quality Report

[Filters] [Options ▼] [Print] [Tasks ▼]     [Search 🔍]

| Lab | Order Id / Uploaded On | AI Status | AI Score | QC Rating | Reason | | |
|---|---|---|---|---|---|---|---|
| | 08/27/2021 10:30:36 | Good | 0.31 | Manageable | | 📄 | ➡ |
| | 08/27/2021 10:27:16 | Good | 0.72 | Good | | 📄 | ➡ |
| | 08/27/2021 10:09:46 | Bad | 0.45 | Manageable | | 📄 | ➡ |
| | 08/27/2021 10:09:36 | Good | 0 | Manageable | | 📄 | ➡ |
| | 08/27/2021 09:58:23 | Good | 0.67 | Perfect | | 📄 | ➡ |
| | 08/27/2021 09:57:04 | Good | 1.00 | Perfect | | 📄 | ➡ |

Rows: 1-100 of ⓘ

METHODS AND SYSTEMS FOR BI-DIRECTIONAL INTEGRATION BETWEEN AN INTRAORAL SCANNER AND A DENTAL LAB

FIELD

This disclosure relates generally to dental management methods and systems between one or more dental offices and one or more dental labs. More specifically, this disclosure relates to methods and systems for providing bi-directional integration between one or more intraoral scanners and one or more dental labs.

BACKGROUND

Dental offices, dental laboratories and dental service organizations (DSOs) typically work together to prepare dental products for patients. These dental products can include, for example, crowns, bridges, dentures, dental implants, orthodontics, dental restorations, etc.

To order a dental product, one or more staff members at a dental office accesses an online web portal for the dental lab they want to prepare the product, fills out a dental product order form using the dental lab web portal, and attaches any additional information (e.g., a dental product prescription, X-rays, photos, etc.) that may be needed by the dental lab. When the dental lab receives the dental product order, a lab technician reviews the information, fabricates the dental product, and mails the product back to the dental office.

SUMMARY

This disclosure relates generally to dental management methods and systems between one or more dental offices and one or more dental labs. More specifically, this disclosure relates to methods and systems for providing bi-directional integration between one or more intraoral scanners and one or more dental labs.

In particular, the embodiments described herein can provide chairside quality control in which a scanned image of a patient taken by an intraoral scanner at a dental office can undergo a quality check in real time so that an operator (e.g., dentist, dental hygienist, technician, etc.) taking the scan can receive real time feedback on whether the scan is of sufficient quality to fabricate the desired dental product. In some embodiments, the real time feedback can be provided directly to the intraoral scanner used to generate the scanned image. In some embodiments, the quality check can be performed in real time by an artificial intelligence engine within minutes of the scan being taken by the operator using the intraoral scanner. Accordingly, re-appointments for the patient and delays in fabricating the dental product can be avoided. That is, a patient can leave the dental office knowing that the scan can be used to fabricate the desired dental product and can be appraised of when the product will be completed. Also, a dental office is not required to perform robotic process automation (RPA) to download scans taken from individual intraoral scanners.

The embodiments described herein can also allow an operator to create an automated dental product prescription from an intraoral scanner by integrating a dental product management platform that connects the intraoral scanner with one or more dental lab(s) used for fabricating the desired dental product. Accordingly, a dental office is not required to submit a dental product prescription directly to a web portal of a desired dental lab. Also, these embodiments can provide dental lab standardization for digital and non-digital dental product orders across all participating dental offices and dental labs. Further these embodiments can embed dental product prescription creation into the intraoral scanner and ensure prescription compliance to produce quality dental products. Thus, the dental office can use any prescription software available on the intraoral scanner and the dental product management platform can convert the prescription into a dental product order in a format that is usable by the dental lab accepting the dental product order.

Accordingly, the embodiments described herein can provide instant and direct access for an operator to scans taken by an intraoral scanner, dental product order creation, and dental product order submission from the intraoral scanner.

The embodiments described herein can provide a platform to facilitate efficiency between one or more dental offices, one or more dental labs and one or more dental service organizations (DSOs).

The embodiments described herein can allow a dental product management platform that is located remotely from an intraoral scanner at a dental office to validate scanned image data received from the intraoral scanner in real time (e.g., while the patient is still at the dental office and possibly still in a dental chair) to determine whether the scan is of acceptable quality to fabricate a dental product.

The dental product management platform can connect one or more intraoral scanners and one or more dental lab management systems while providing quality control to validate scanned image data received from any of the one or more intraoral scanners.

In some embodiments, the dental product management platform can receive metadata that includes prescription information from the intraoral scanner and use the prescription information for a dental product order sent by the dental product management platform to a dental lab for fabrication of a dental product.

In some embodiments, the dental product management platform can receive/pull scanned image data and prescription information from an intraoral scanner instantly, review the scanned image data, and validate the scanned image data in near real-time (e.g., within 20 minutes, while the patient is in a dental chair at the dental office, etc.).

In some embodiments, the dental product management platform can integrate with different intraoral scanner software portals and can integrate with different dental lab software portals. Accordingly, the dental product management platform can reduce delays in receiving, formatting and sending information between an intraoral scanner and a dental lab.

In some embodiments, the dental product management platform can validate scanned image data using an automated process. In some embodiments, the automated process can use artificial intelligence (AI).

In one embodiment, a method for bi-directional integration between one or more intraoral scanners and one or more dental labs is provided. The method includes a dental product management platform receiving an instruction to create a new dental product prescription from an operator via a graphical user interface of the dental product management platform provided on a particular intraoral scanner of the one or more intraoral scanners. The method also includes the dental product management platform creating the new dental product prescription. Also, the method includes the dental product management platform receiving prescription information from the operator via the graphical user interface. Further, the method includes the dental product management platform receiving scanned image data from the particular intraoral scanner, the scanned image data being obtained from a scan of a patient performed by the particular intraoral scanner. The method further includes the dental product management platform creating a new dental product order based on the new dental product prescription and the scanned image data. Moreover, the method includes the dental product management platform validating the scanned image data in real time to determine whether the scan is of acceptable quality to fabricate a dental product that meets the requirements of the dental product prescription. Upon determining that the scanned image data is of acceptable quality, the dental product management platform: allocating the new dental product order to the dental lab, sending the new dental product order that includes the new dental product prescription and the scanned image data to the dental lab. Upon determining that the scanned image data is not of acceptable quality, the dental product management platform provides a notification to the operator via the graphical user interface to use the particular intraoral scanner to take a second scan of the patient using the particular intraoral scanner.

In another embodiment, a dental product management system configured to provide bi-directional integration between one or more intraoral scanners and one or more dental labs is provided. The dental product management system includes a dental product management platform that includes a graphical user interface accessible by a particular intraoral scanner of the one or more intraoral scanners. The dental product management platform is configured to: receive an instruction to create a new dental product prescription from an operator via a graphical user interface of the dental product management platform provided on a particular intraoral scanner of the one or more intraoral scanners; create the new dental product prescription; receive prescription information from the operator via the graphical user interface; receive scanned image data from the particular intraoral scanner, the scanned image data being obtained from a scan of a patient performed by the particular intraoral scanner; create a new dental product order based on the new dental product prescription and the scanned image data; and validate the scanned image data in real time to determine whether the scan is of acceptable quality to fabricate a dental product that meets the requirements of the dental product prescription. Upon determining that the scanned image data is of acceptable quality, the dental product management system is configured to: allocate the new dental product order to the dental lab, and send the new dental product order that includes the new dental product prescription and the scanned image data to the dental lab. Upon determining that the scanned image data is not of acceptable, the dental product management system is configured to: provide a notification to the operator via the graphical user interface to use the particular intraoral scanner to take a second scan of the patient using the particular intraoral scanner.

BRIEF DESCRIPTION OF THE DRAWINGS

References are made to the accompanying drawings that form a part of this disclosure, and which illustrate embodiments in which the systems and methods described in this Specification can be practiced.

FIG. 3 illustrates a screenshot of a GUI provided by the dental product management platform for display on the computer, according to one embodiment.

Like reference numbers represent like parts throughout.

DETAILED DESCRIPTION

This disclosure relates generally to dental management methods and systems between one or more dental offices and one or more dental labs. More specifically, this disclosure relates to methods and systems for providing bi-directional integration between one or more intraoral scanners and one or more dental labs.

It is noted that: U.S. application Ser. No. 18/189,828, "METHODS AND SYSTEMS FOR INTEGRATED DESIGN WORKFLOW BETWEEN AN INTRAORAL SCANNER, A DESIGN SERVICE AND A MILLING CENTER,"; and U.S. application Ser. No. 18/189,832, "METHODS AND SYSTEMS FOR FINANCIAL MANAGEMENT AND RECONCILIATION WITHIN A DENTAL PROJECT MANAGEMENT SYSTEM,"; all filed concurrently herewith on Mar. 24, 2023, and the contents of which are incorporated herein by reference.

Figure 1:
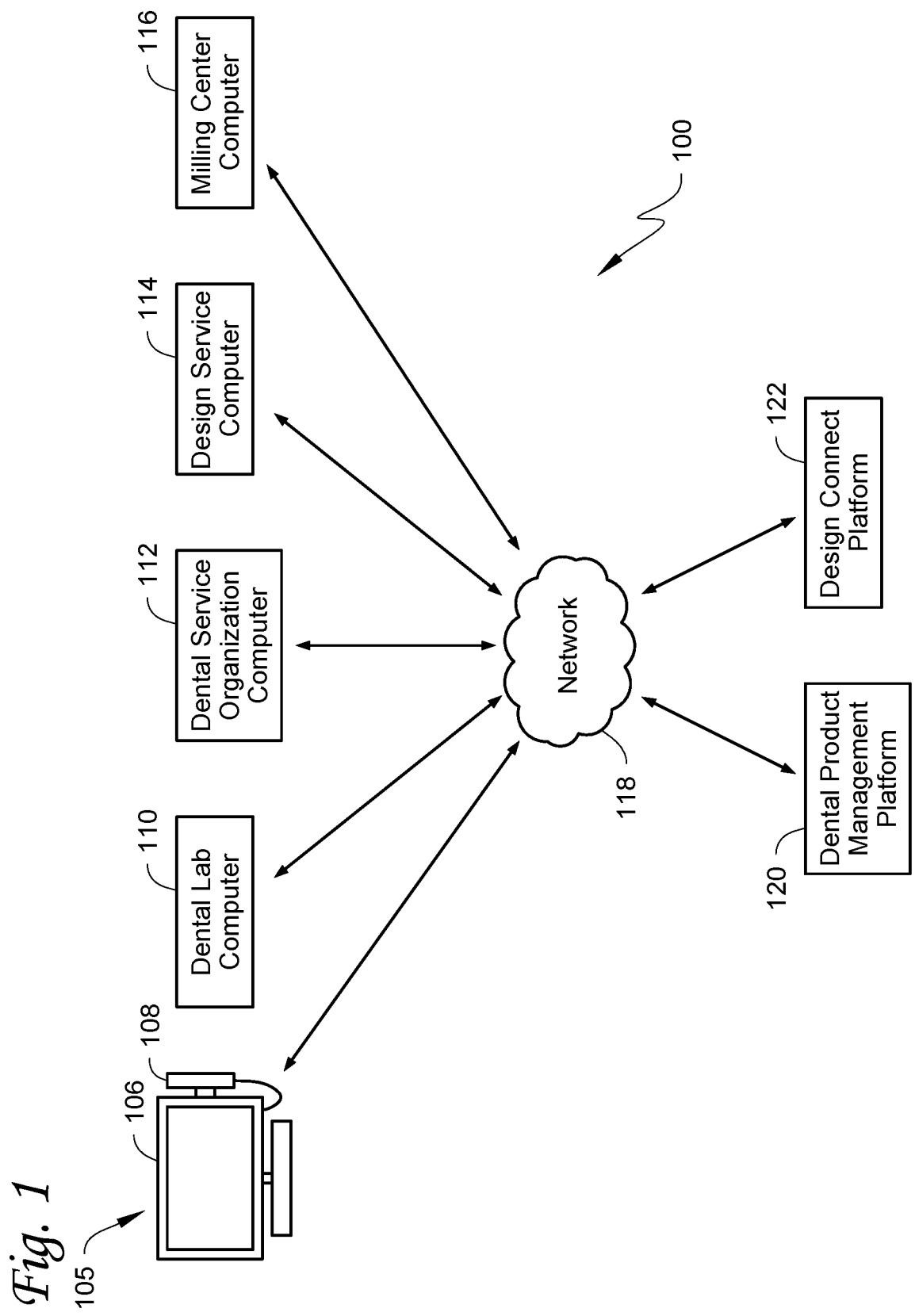
FIG. 1 illustrates a dental product management system, according to one embodiment.

FIG. 1 illustrates a dental product management system 100, according to one embodiment. The system 100 includes an intraoral scanner 105 at a dental office, a dental lab computer 110 at a dental lab, a dental service organization (DSO) computer 112 at a DSO that are connected to a dental product management platform 120 via a network 118. The system 100 also includes a design service computer 114 and a milling center computer 116 connected to a design connect platform 122 via the network 118. The dental product management platform 120 is connected to the design connect platform 122 via the network 118. It will be appreciated that while only a single intraoral scanner, dental lab, DSO, design service and milling center are shown in FIG. 1, in other embodiments there may be multiple intraoral scanners, dental labs and/or DSOs connected to the dental product management platform 120 and there may be multiple design services and/or milling centers connected to the design connect platform 122.

The intraoral scanner 105 is an electronic device configured to obtain image data (e.g., 3D image data) of anatomical structures within the mouth of a patient. The image data can be used to create a dental product such as, for example, a crown, bridge, denture, dental implant, orthodontic, dental restoration, etc. The intraoral scanner 105 can be located at, for example, a dental office. The intraoral scanner 105 includes a computer 106 and a wand 108. An operator (e.g., dentist, dental hygienist, technician, etc.) at a dental office can use the wand 108 to scan a patient's mouth to obtain image data. The computer 106 can include one or more processors for both controlling operation of the wand 108, including coordinating the scanning and in reviewing and processing the scanning and generation of the image data including surface and internal features. The one or more processors may include or may be coupled with a memory for storing the scanned image data (surface data, internal feature data, etc.). The computer 106 can include one or more inputs (e.g., buttons, touchscreen, keyboard, etc.) to allow operator input for controlling scanning and operation of the intraoral scanner 105. Also, the computer 106 can include a display for allowing the operator to view the scanned image data and other information related to operation of the intraoral scanner 105. The computer 106 can also include communications circuitry, including wireless or wired communications circuitry, for communicating with the wand 108 and/or accessing the dental product management platform 120 via network 118. For example, the computer 106 may be configured to allow the operator to prepare a dental product prescription and combine scanned image data with the dental product prescription using the dental product management platform 120. The computer 106 can be the same as or similar to aspects of the computer device 500 as shown and described in accordance with FIG. 6 below.

The dental lab computer 110 is a computer at a dental lab that is configured to receive dental product prescriptions with scanned image data, fabricate a desired dental product as requested in the dental product prescription, and provide the fabricated dental product to the desired recipient (e.g., a dental office where the intraoral scanner 105 is located). In some embodiments, the dental lab computer 110 is at a location different from the location of the intraoral scanner 105. The dental lab computer 110 is configured to access the dental product management platform 120 via the network 118 to, for example, receive dental product prescriptions and scanned image data. The dental lab computer 110 can be the same as or similar to aspects of the computer device 500 as shown and described in accordance with FIG. 6 below.

The DSO computer 112 is a computer of a DSO that is configured to provide business management and support for one or more dental offices including a dental office where the intraoral scanner is located. In some embodiments, the DSO computer 112 is at a location different from the locations of the intraoral scanner 105 and the dental lab computer 110. The DSO computer 112 is configured to access the dental product management platform 120 via the network 118 to, for example, track dental product management status between one or more dental offices and one or more dental labs, verify and approve invoicing between one or more dental offices and one or more dental labs, obtain quality analysis of dental product orders, obtain dental product orders volume analysis, obtain purchase value analysis of the dental product orders, obtain turnaround time for dental product orders for the one or more dental labs, obtain benchmarking analysis of the dental product orders, etc. The DSO computer 112 can be the same as or similar to aspects of the computer device 500 as shown and described in accordance with FIG. 6 below.

Figure 2:
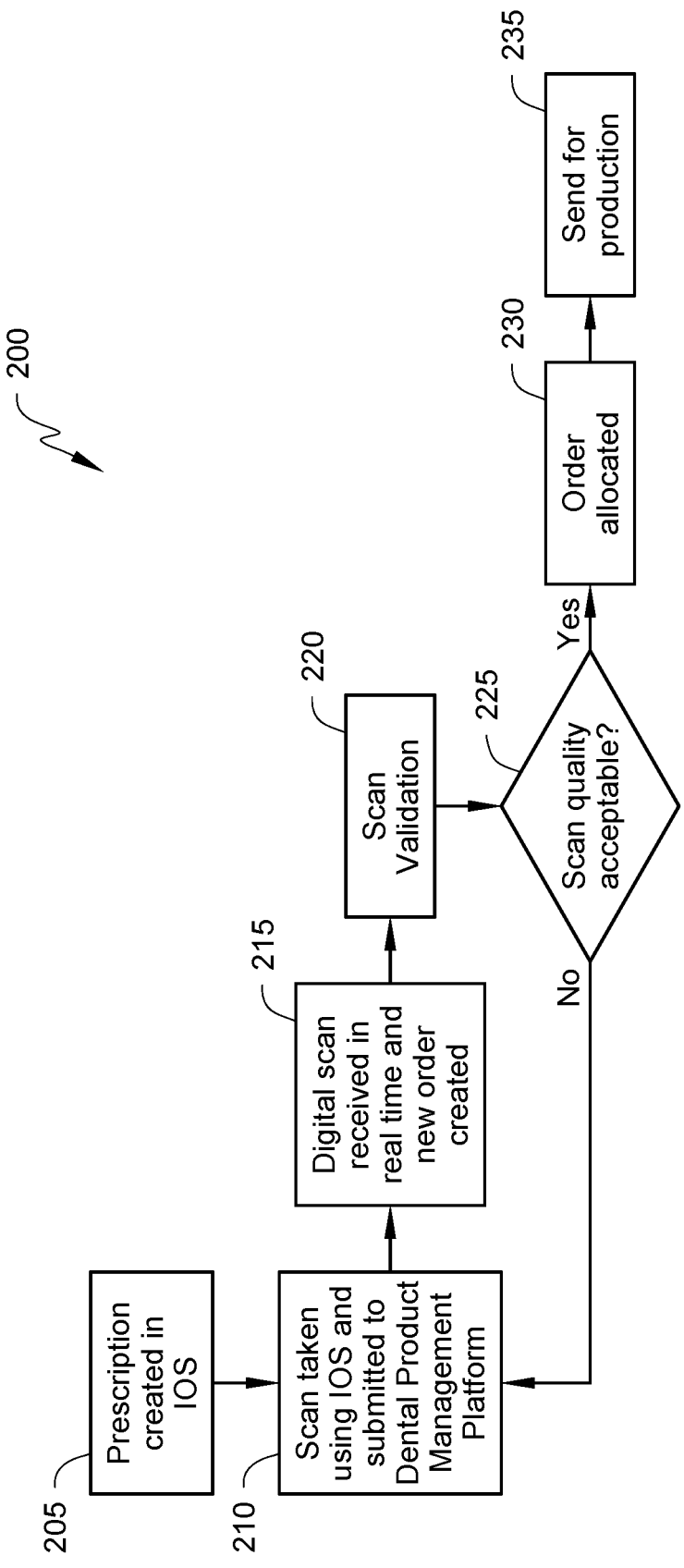
FIG. 2 illustrates a flowchart of a method for providing bi-directional intraoral scanner integration between the intraoral scanner and the dental lab computer, according to one embodiment.
Figure 4:
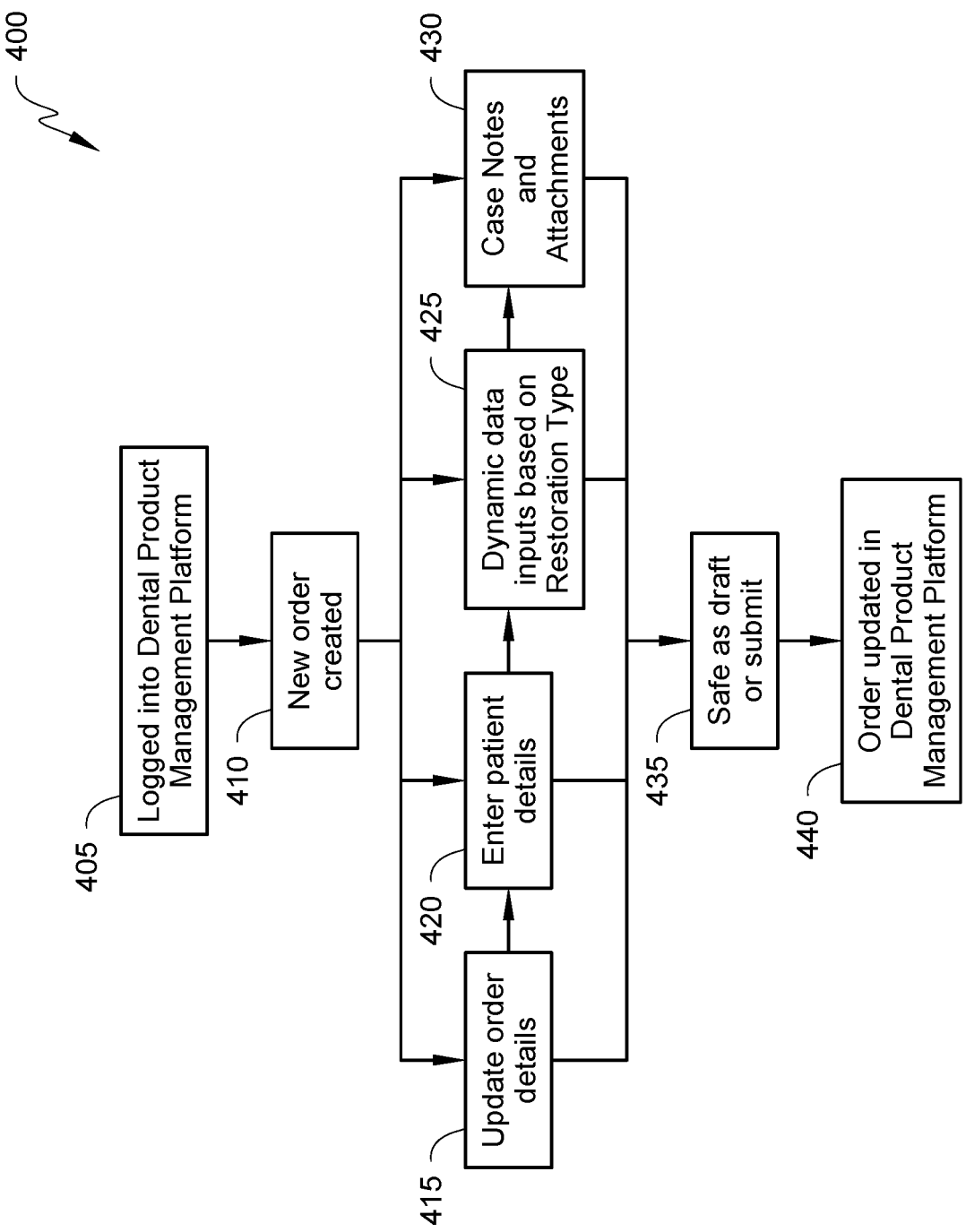
FIG. 4 illustrates a flowchart of a method of creating new dental product order, according to one embodiment.

The dental product management platform 120 is configured to provide an online management platform that can connect one or more dental offices (e.g., via an intraoral scanner), one or more dental labs, and one or more DSOs. The intraoral scanner 105, the dental lab computer 110, and the DSO computer 112 can access the dental product management platform 120 via, for example, a graphical user interface (GUI) accessible via a website and/or online software application. The dental product management platform 120 can include one or more application programming interfaces (APIs) that enable, for example, bi-directional intraoral scanner integration between the intraoral scanner 105 and the dental lab computer 110 (as shown in FIG. 2 and described in more detail below); prescription standardization across digital and non-digitized dental product prescriptions across all participating dental offices and dental labs (as shown in FIG. 4 and described in more detail below); financial reconciliation from an initial patient visit through a dental office dental product prescription creation, manufacturing lab invoice with dental product order sign off, and DSO payment reconciliation; and interactive voice response (IVRS) to provide order specific and lab specific information on a dental product order, shipment, invoice, billing statuses, etc. In some embodiments, the dental product management platform 120 can be supported by one or more servers similar to the server device 535 shown and described in accordance with FIG. 6 below. The dental product management platform 120 is also configured to communicate with the design connect platform 122. In some embodiments, the dental product management platform 120 and the design connect platform 122 are part of the same platform. For example, in some embodiments the dental product management platform 120 can be connected to the design connect platform 122 via an interface layer. In some embodiments, the dental product management platform 120 can be a cloud based application platform.

The design service computer 114 is a computer configured to provide designer services to design a dental product. In some embodiments, the design service computer 114 is a computer of a design service that is configured to provide designer services for one or more dental offices including a dental office where the intraoral scanner is located. In some embodiments, the design service computer 114 is at a location different from the locations of the intraoral scanner 105 and the dental lab computer 110. In some embodiments, the design computer 114 can be located at a dental office where the intraoral scanner 105 is located. In some embodiments, the design computer 114 can be located at a design center where the dental lab computer 110 is located. The design service computer 114 is configured to access the design connect platform 122 via the network 118 to, for example, obtain dental product order(s) with a dental product prescription and scanned image data to allow a designer to generate a design of the desired dental product. The design service computer 114 can be the same as or similar to aspects of the computer device 500 as shown and described in accordance with FIG. 6 below.

The milling center computer 116 is a computer of a milling center that is configured to provide milling services for one or more dental offices including a dental office where the intraoral scanner is located. In some embodiments, the milling center computer 116 can be located where the design computer 114 is located. In some embodiments, the milling center computer 116 is at a location different from the locations of the intraoral scanner 105, the dental lab computer 110, and potentially the design service computer 114. The milling center computer 116 is configured to access the design connect platform 122 via the network 118 to, for example, obtain a generated design of the dental product to allow the milling service to fabricate the desired dental product. In some embodiments, the milling center computer 116 can be configured to access the design connect platform 122 via the network 118 to, for example, obtain dental product order(s) with a dental product prescription and scanned image data to allow a designer at the milling center to generate a design of the desired dental product and then allow the milling service to fabricate the desired dental product. In some embodiments, the milling center computer 116 can be configured to access the dental product management platform 120 via the network 118 to, for example, obtain dental product order(s) with a dental product prescription and scanned image data directly from, for example, the intraoral scanner 105 to allow a designer at the milling center to generate a design of the desired dental product and then allow the milling service to fabricate the desired dental product. The milling center computer 116 can be the same as or similar to aspects of the computer device 500 as shown and described in accordance with FIG. 6 below.

The design connect platform 122 is configured to provide an online design platform that can connect one or more dental labs, one or more design services and one or more milling services. The dental lab computer 110, the design service computer 114 and the milling center computer 116 can access the design connect platform 122 via, for example, a graphical user interface (GUI) accessible via a website and/or online software application. The design connect platform 122 can enable, for example, an integrated design workflow and manufacturing from the dental lab (via the dental lab computer 110) to the design service (via the design service computer 114) and to the milling center (via the milling center computer 116); tracking dental product order(s); real time turnaround time and quality analysis reports; etc. Accordingly, a design center having the design service computer 114 can use the design connect platform 122 to manage design services. In some embodiments, the dental product management platform 120 can be supported by one or more servers similar to the server device 535 shown and described in accordance with FIG. 6 below. The design connect platform 122 is also configured to communicate with the dental product management platform 120. In some embodiments, the design connect platform 122 can interact with the dental product management platform 120 to access dental product orders submitted by, for example, the intraoral scanner 105. In some embodiments, the dental product management platform 120 and the design connect platform 122 are part of the same platform. In some embodiments, the dental product management platform 120 can be a cloud based application platform.

In an embodiment, the network 118 is representative of the Internet. In an embodiment, the network 40 can include one or more local area networks (LANs), one or more wide area networks (WANs), one or more wireless networks, one or more cellular data networks, suitable combinations thereof, or the like. In an embodiment, aspects of the network 118 can be the same as or similar to aspects of the network 540 as shown and described in accordance with FIG. 6 below.

FIG. 2 illustrates a flowchart of a method 200 for providing bi-directional intraoral scanner integration between the intraoral scanner 105 and the dental lab computer 110, according to one embodiment. The method 200 begins at 205 whereby a dental product prescription is created via the intraoral scanner 105. In particular, an operator (e.g., dentist, dental hygienist, technician, etc.) can create a new dental product prescription using a GUI of the dental product management platform 120 via the computer 106. The dental product prescription can include prescription information including, for example, dental product order details (e.g., restoration type, tooth number, material, shade, stump shade, etc.), patient details, data based on a restoration type, case notes and attachments, etc. The dental product management platform 120 includes an application programming interface (API) that allows the operator to create and enter relevant information for the dental product prescription using the GUI of the dental product management platform 120. A method for creating a new dental product prescription is discussed below with respect to FIG. 4. Once the dental product prescription is created within the dental product management system, the method 200 proceeds to 210.

At 210, the operator takes a scan using the wand 108 of the intraoral scanner 105 and the computer 106 submits the dental product prescription created at 205 with scanned image data from the scan in real time to the dental product management platform 120 with the dental product prescription created at 205. The method 200 then proceeds to 215.

At 215, the dental product management platform 120 receives the dental product prescription and the scanned image data in real time and creates a new dental product order for use, for example, by a dental lab (via the dental lab computer 110). The method 200 then proceeds to 220.

At 220, the dental product management platform 120 validates the scanned image data to determine whether it is of acceptable quality to be able to create the dental product and notifies the operator if the scanned image data is acceptable. In some embodiments, the dental product management platform 120 can use an artificial intelligence (AI) based scan validation in real time. In particular, the dental product management platform 120 can analyze the scanned image data to review, for example, scan visibility, margin(s), undercut(s), bite visibility, ditch, etc. Based on an analysis of these parameters, the dental product management platform 120 can determine whether the scanned image data is of sufficient quality to be able to create the dental product. In some embodiments, the AI based scan validation can score the scanned image data (e.g., between 0 and 1) and categorizes the scanned image data in various categories (e.g., bad, manageable, good, and perfect). If the score of the scanned image data is below a required threshold level in which the scanned image data cannot be used to create a dental product, the scanned image data can be categorized as bad. In some embodiments, if the score of the scanned image is above the required threshold level but is below a recommended threshold level (e.g., a score that categorizes the scanned image data as manageable—that is a score between good and bad), the dental product management platform 120 sends a notification to a dental lab to conduct a manual (e.g., human review) of the scanned image data to verify whether the scanned image data is acceptable.

The dental product management platform 120 also notifies the operator whether the scanned image data is acceptable for fabricating a dental product as per the dental product prescription. In some embodiments, the dental product management platform 120 can notify the operator whether the scanned image data is acceptable via the GUI displayed on a display screen of the computer 106. For example, FIG. 3 illustrates a screenshot 300 of a GUI provided by the dental product management platform 120 for display on the computer 106 indicating whether the scanned image data is acceptable for fabricating a dental product as per the dental product prescription, according to one embodiment.

As shown in FIG. 3, the screenshot 300 includes rows of scanned image data results 255 and columns of information for each of the rows. The columns of information include a dental lab column 260 indicating an assigned dental lab to the particular dental product order, an order identification number column 262, an upload date column 264 indicating when the scanned image data was uploaded to the dental product management platform 120, a status column 266 of the scanned image data, a score column 268 of the scanned image data, a quality control rating column 270 of the scanned image data, an additional information column 272, a PDF link column 274, and a download link column 276. The dental lab column 260 and the order identification number column 262 can be empty until a dental lab is assigned to the particular dental product order corresponding to the scanned image data result 255a-e. The status column 266 indicates the status result of each of the scanned image data results 255 including Good and Bad. The score column 268 indicates the score result of each of the scanned image data results 255 from 0 to 1 obtained at 220. The quality control rating column 270 indicates the category result of each of the scanned image data results 255 including Bad, Manageable, Good, and Perfect obtained at 220. The additional information column 272 can include reasons for a particular status, score or quality control rating that can assist the operator when, for example, taking another scan. The PDF link column 274 allows the operator to view the information of a particular scanned image data result 255 in a PDF file. The download link column 276 allows the operator to download the information of a particular scanned image data result 255 onto the computer 106 or another computer device that has access to the data product management system 120.

Returning to FIG. 2, the method 200 can proceed from the operator taking a scan using the wand 108 and submitting the scanned image data to the dental product management platform 120 at 210 to validating the scanned image data and notifying the operator if the scanned image data is acceptable at 220 within twenty minutes or less. Accordingly, the method 200 can provide chair side quality control whereby the operator is provided near real-time scan feedback. This can prevent the need for a re-appointment with the patient and further delays in fabricating a dental product. The method 200 then proceeds to 225.

At 225, if the dental product management platform 120 determines that the scanned image data is of sufficient quality for creating the desired dental product as provided in the dental product prescription (e.g., the score of the scanned image data is at or above a required threshold level), the method 200 proceeds to 230. If the dental product management platform 120 determines that the scanned image data is not of sufficient quality for creating the desired dental product as provided in the dental product prescription (e.g., the score of the scanned image data is below a required threshold level) the dental product management platform 120 provides a notification to the operator via the GUI displayed on the computer 106 of the intraoral scanner 105 and the method 200 proceeds back to 210 where the operator can take another scan. The notification can indicate that the scan was not of sufficient quality and request the operator to take another scan while the patient is still at the dental office.

At 230, the dental product management platform 120 allocates the new dental product order to a particular dental lab. In some embodiments, the dental product management platform 120 can allocate the new dental product order automatically based on a complexity of the order and a skill set of the design service. For example, the dental product management platform 120 can route the new dental product order to the design management platform 122. When the new dental product order is available in the design management platform 122, the new dental product order can be allocated to a respective designer depending on the type of order, skill level required, etc. In some embodiments, the dental product management platform 120 can allocate the new dental product order based on input from the operator. The method 200 then proceeds to 235.

At 235, the dental product management platform 120 sends the new dental product order to the dental lab identified at 230 for production in order to complete the dental product order. In some embodiments, where a dental lab can design and fabricate a dental product order (e.g., includes both a design service computer 114 and a milling center computer 116) the dental product management platform 120 can post the new dental product order directly to the dental lab for design and manufacturing through, for example, the design connect platform 122. In some embodiments, where a dental lab can design a dental product order (via the design service computer 114) but not fabricate the dental product, the dental product management platform 120 can post the new dental product order directly to the dental lab for design through, for example, the design connect platform 122 and then the dental lab can post the design to the design connect platform 122 for access by a separate milling center (via the milling center computer 116) for fabrication.

The method 200 allows the dental product management platform 120 to provide chairside quality control in which a scanned image of a patient taken by the intraoral scanner 105 at a dental office can undergo a quality check in real time so that an operator taking the scan can receive real time feedback on whether the scan is of sufficient quality to fabricate the desired dental product. The method 200 can also allow the quality check to be performed in real time by an artificial intelligence engine operating under the dental product management platform 120 within minutes of the scan being taken by the operator using the intraoral scanner 105. Accordingly, re-appointments for the patient and delays in fabricating the dental product can be avoided. Also, a dental office is not required to perform robotic process automation (RPA) to download scans taken from individual intraoral scanners.

FIG. 4 illustrates a flowchart of a method 400 of creating new dental product order, according to one embodiment. In some embodiments, an operator can provide information for the method 400 to create the new dental product order using the computer 106 of the intraoral scanner 105.

The method 400 beings at 405 whereby the dental product management platform 120 receives login information from an operator (e.g., dentist, dental hygienist, technician, etc.) for logging into the dental product management platform 120. In some embodiments, the operator can log into the dental product management platform 120 via the computer 106 of the intraoral scanner 105. Logging into the dental product management platform 120 can include, for example, the operator entering a username and password that associates the operator with an account of the dental product management platform 120. Once the operator is logged into dental the product management platform 120, the method 400 proceeds to 410.

At 410, the dental product management platform 120 creates a new dental product prescription for storage into the dental product management platform 120. In some embodiments, the dental product management platform 120 receives an instruction from the operator, via a GUI of the dental product management platform 120, to create the new dental product prescription. Upon creation of the new dental product prescription, the dental product management platform 120 provides an API on the GUI that allows the operator to create and enter relevant information for the dental product prescription. The method 410 then proceeds either sequentially through 415, 420, 425, 430 or concurrently through 415, 420, 425 and 430.

At 415, the dental product management platform 120 receives and stores, via information provided by the operator using the GUI of the dental product management platform 120, order details regarding the new dental product prescription. This can include, for example, information regarding the dental lab requested by the operator to handle the dental product order, information regarding the dental office creating the dental product order, information regarding whether the dental product order is a rush order, information regarding whether the dental product order is a remake of a previous dental product order, a due date for completing the dental product order, a shipping address for which the finished dental product is to be shipped, etc.

At 420, the dental product management platform 120 receives, via information provided by the operator using the GUI of the dental product management platform 120, and stores patient details regarding the new dental product prescription. This can include, for example, the patient's first name, last name, patient identification number, gender, age, etc.

At 425, the dental product management platform 120 receives from the operator, by using the GUI, dynamic data inputs based on a restoration type using the GUI of the dental product management platform 120. This can include, for example, a prosthesis type, a restoration type, an indication, a material type, a material name, a shade guide, shade comment(s), etc. For example, for a fixed restoration type the dynamic data inputs can include, for example, tooth number wise shades, material type, indication, etc. For example, for a removable restoration type, the dynamic data inputs can include, for example, full or partial prosthesis type, material, additional remarks, etc.

At 430, the dental product management platform 120 receives from the operator, by using the GUI of the dental product management platform 120, order notes and attachments. This can include instructions related to the restoration that is required. The attachments can include, for example, reference images and/or reference documents. Once 415, 420, 425 and 430 are completed, the method 400 proceeds to 435.

At 435, the dental product management platform 120 receives instructions from the operator, via the GUI of the dental product management platform 120, to either save a draft of the new dental product prescription or to submit the new dental production prescription to the dental lab 110. The method 400 then proceeds to 440.

At 440, upon receipt of instructions from the operator at 435, the dental product management platform 120 is configured to update the new dental product prescription stored in the dental product management platform 120. This can include the dental product management platform updating the dental product prescription created by the operator into a format required by the dental lab selected by the operator at 415. In some embodiments, the new dental product prescription can update the new dental product prescription in the dental product management platform 120 in real time. The method 400 then proceeds to 440.

Accordingly, the method 400 allows an operator to create an automated dental product prescription from the intraoral scanner 105 by integrating the dental product management platform 120 that connects the intraoral scanner 105 with one or more dental lab(s) 110 used for fabricating the desired dental product. Accordingly, a dental office is not required to submit a dental product prescription directly to a web portal of a desired dental lab. Also, these embodiments can provide dental lab standardization for digital and non-digital dental product orders across all participating dental offices and dental labs. Further these embodiments can embed dental product prescription creation into the intraoral scanner 105 and ensure prescription compliance to produce quality dental products.

Figure 5A:
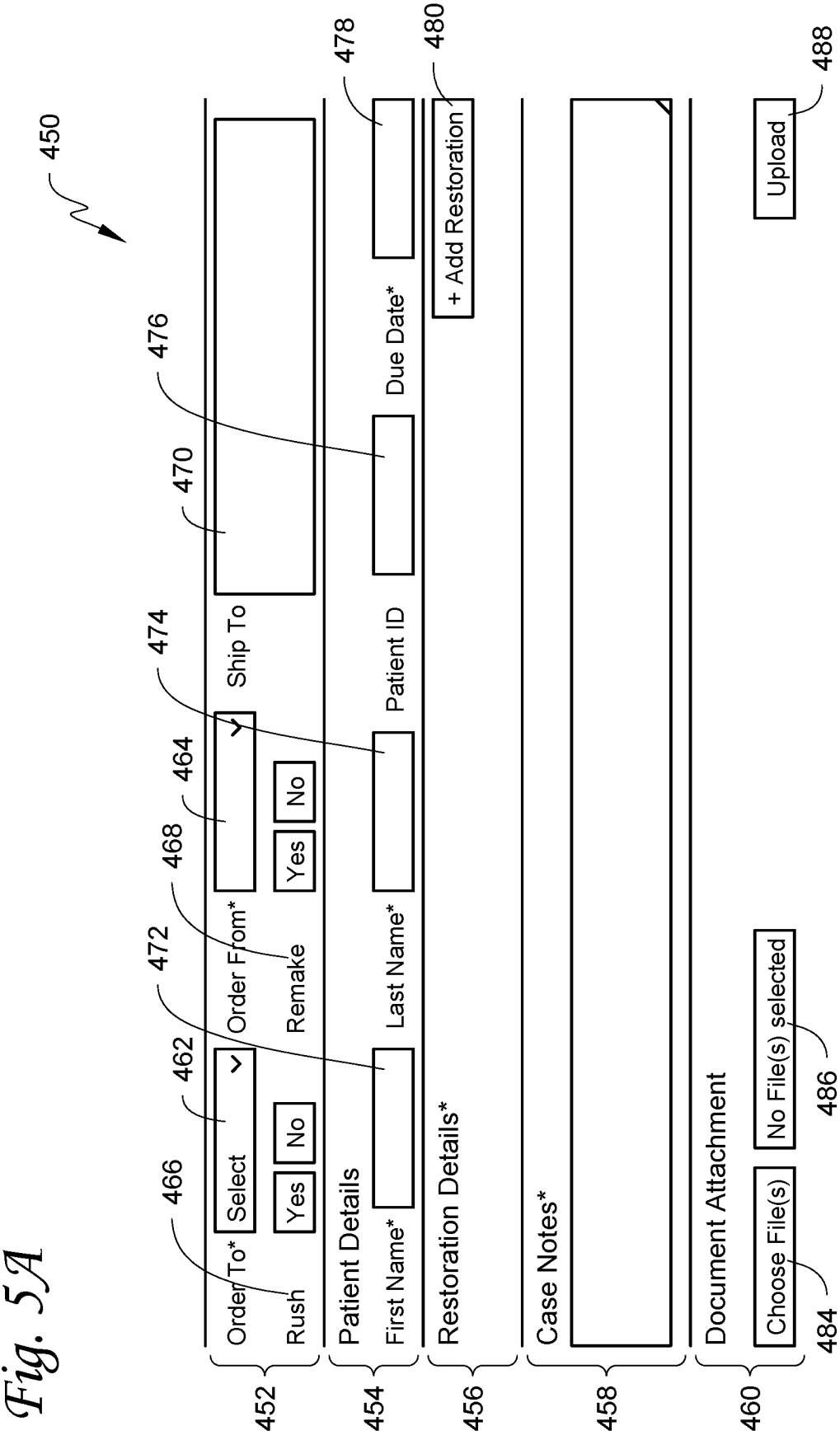
FIG. 5A illustrates a screenshot of a GUI provided by the dental product management platform for display on the computer of the intraoral scanner, according to one embodiment.

FIG. 5A illustrates a screenshot 450 of a GUI provided by the dental product management platform 120 for display on the computer 106 of the intraoral scanner, according to one embodiment. In particular, the screenshot 450 shows what the dental project management platform 120 displays when the operator is creating a new dental product prescription (e.g., entering information at 415, 420, 425 and 430 of the method 400).

The screenshot 450 includes an order details section 452, a patient details section 454, a restoration section 456, a case notes section 458, and a document attachment section 460. The order details section 452 allows an operator to select a dental lab to handle the dental product order at 462, select the dental office creating the dental product order at 464, select whether the dental product order is a rush order at 466, select whether the dental product order is a remake of a previous dental product order at 468, and enter a shipping address for which the finished dental product is to be shipped at 470.

The patient details section 454 allows an operator to enter the first name of the patient at 472, enter the last name of the patient at 474, enter a patient identification number associated with the patent at 476, and enter a due date for completing the dental product order at 478.

Figure 5B:
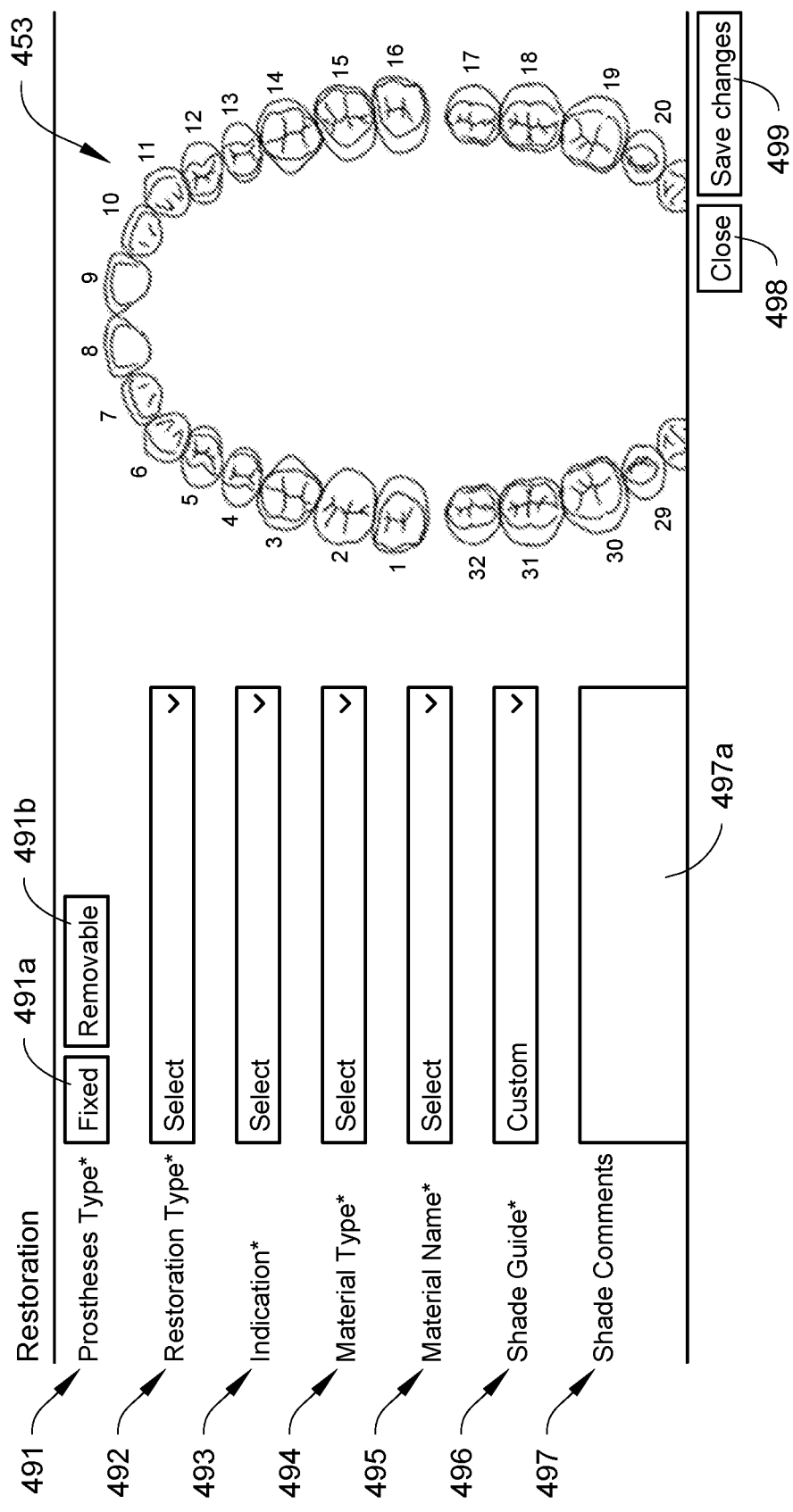
FIG. 5B illustrates another screenshot of a GUI provided by the dental product management platform for display on the computer of the intraoral scanner, according to one embodiment.

The restoration section 456 allows an operator to add a new restoration via an add restoration link 480. Upon selection of the restoration link 480, the dental product platform 120 displays a screenshot 490 shown, for example, in FIG. 5B of the GUI provided by the dental product management platform 120 for providing dynamic data inputs based on a restoration type selected by the operator. As shown in FIG. 5B, the screenshot 490 includes prosthesis type links 491, a restoration type menu 492, an indication menu 493, a material type menu 494, a material name menu 495, a shade guide menu 496 and a shade comments section 497.

The prosthesis type links 491 allows an operator to select between either a fixed prosthesis type via link 491a or a removable prosthesis type via link 491b. The restoration type menu 492 allows an operator to select between different restoration types (e.g., ceramic, porcelain fused metal/full cast/partial cast metal, implant products, etc. The indication menu 493 allows an operator to select between different indications (e.g., crown, bridge, veneer, inlay/onlay, etc. The material type menu 494 allows an operator to select between different material types (e.g., zirconia, lithium disilicate, leucite glass-ceramic, temporary (acrylic), etc. The material name menu 495 allows an operator to select between different material names once a particular material type is selected. For example, if zirconia is selected at menu 494, the menu 495 can include, for example, Bruxzir—anterior, Bruxzir—posterior, CAC Picasso—anterior, CAC Picasso—posterior, CAC Z.Ceram, full contour high translucent, full contour layered, full contour monolithic anterior, full contour monolithic posterior, etc. The shade guide menu 496 allows an operator to select between different shade guides (e.g., VITA_classical, VITA_3D master, custom, etc. In some embodiments, the selections available for each of the restoration type menu 492, the indication menu 493, the material type menu 494, the material name menu 495 and the shade guide menu 496 can be dynamic and change according to selections made to any of the other of the restoration type menu 492, the indication menu 493, the material type menu 494, the material name menu 495 and the shade guide menu 496. Accordingly, the GUI provided by the dental product management platform 120 can provide dynamic data inputs based on selections made by an operator. That is, the input fields for each of the menus 491-496 can show additional or hidden selections based on details captured and/or selections made by a user for the other menus 491-496. For example, if the user selects a removable prosthesis type via link 491b, then the shade guide menu 496 is not applicable and can be removed or greyed out so that a user cannot make a selection from this menu. The shade comments section 497 includes a text box 497a that allows an operator to provide any shade comments, notes and/or details relevant for the particular dental product order.

The screenshot 490 incudes a close link 498 and a save changes link 499. The close link 498 allows an operator to close the screenshot 490 and return to the screenshot 450 The save changes link 499 allows an operator to save selections made by the operator in the portion of the GUI shown in the screenshot 490. The screenshot 490 also displays an image 453 produced from scanned image data associated with the particular dental product order.

Returning to FIG. 5A, the case notes section 458 allows an operator to provide any additional comments, notes and/or details relevant for the particular dental product order within a text box 482. The document attachment section 460 allows an operator to add a document (e.g., picture files, pdf files, Microsoft Word files, etc.) relevant to the particular dental product order. The document attachment section 460 includes a choose file(s) link 484 that allows an operator to access available file(s) stored in the computer 106, a no file(s) selected icon 486 that indicates whether any documents have been attached, and an upload link 488 that allows an operator to upload any file(s) added to the document attachment section 460 to the dental product management platform 120.

Figure 6:
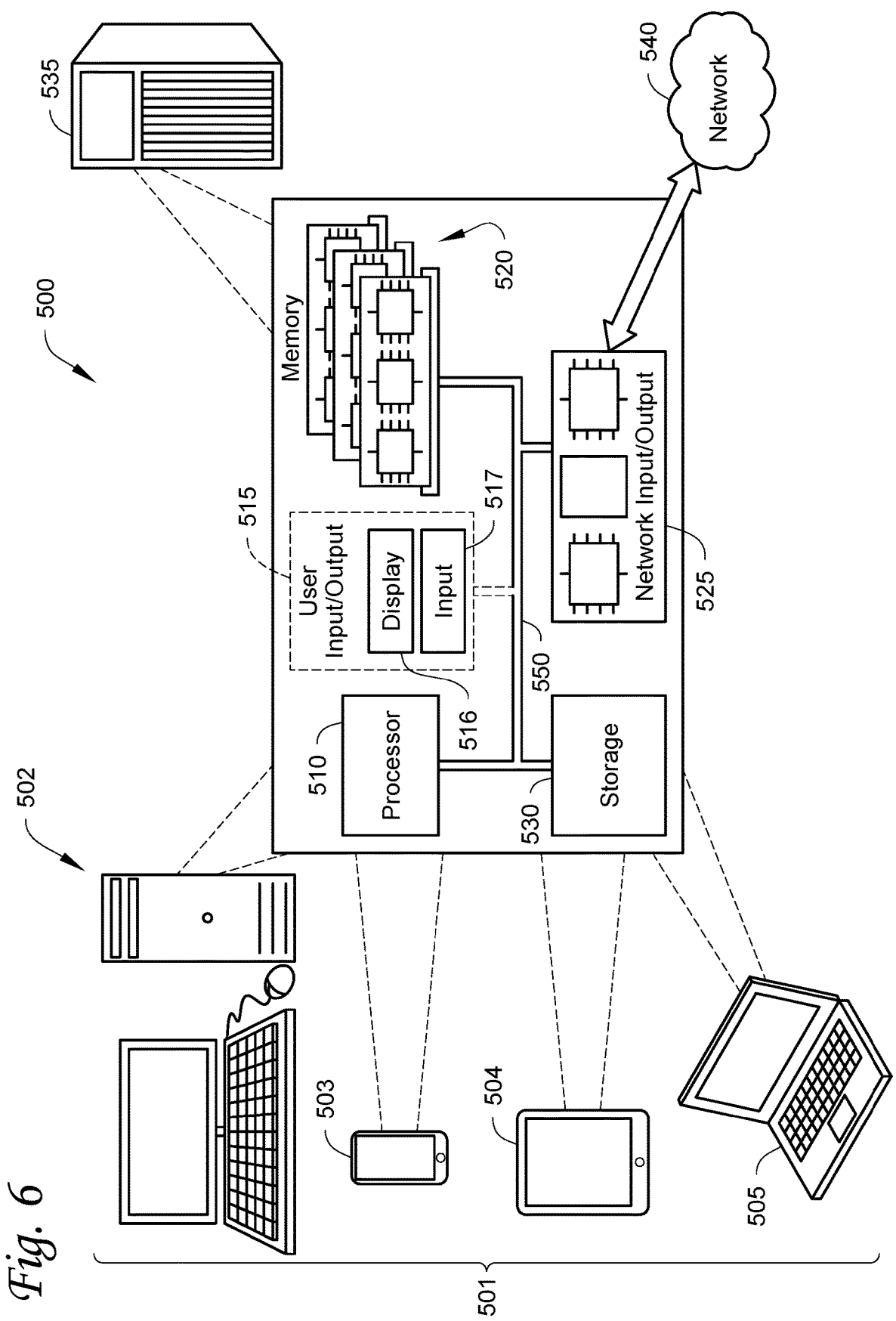
FIG. 6 is a schematic diagram of architecture for a computer device, according to one embodiment.

FIG. 6 is a schematic diagram of architecture for a computer device 500, according to an embodiment. The computer device 500 and any of the individual components thereof can be used for any of the operations described in accordance with any of the computer-implemented methods described herein.

The computer device 500 generally includes a processor 510, memory 520, a network input/output (I/O) 525, storage 530, and an interconnect 550. The computer device 500 can optionally include a user I/O 515, according to some embodiments. The computer device 500 can be in communication with one or more additional computer devices 500 through a network 540.

The computer device 500 is generally representative of hardware aspects of a variety of user devices 501 and a server device 535. The illustrated user devices 501 are examples and are not intended to be limiting. Examples of the user devices 501 include, but are not limited to, a desktop computer 502, a cellular/mobile phone 503, a tablet device 504, and a laptop computer 505. It is to be appreciated that the user devices 501 can include other devices such as, but not limited to, a wearable device, a personal digital assistant (PDA), a video game console, a television, or the like. In an embodiment, the user devices 501 can alternatively be referred to as client devices 501. In such an embodiment, the client devices 501 can be in communication with the server device 535 through the network 540. One or more of the client devices 501 can be in communication with another of the client devices 501 through the network 540 in an embodiment.

The processor 510 can retrieve and execute programming instructions stored in the memory 520 and/or the storage 530. The processor 510 can also store and retrieve application data residing in the memory 520. The interconnect 550 is used to transmit programming instructions and/or application data between the processor 510, the user I/O 515, the memory 520, the storage 530, and the network I/O 540. The interconnect 550 can be, for example, one or more busses or the like. The processor 510 can be a single processor, multiple processors, or a single processor having multiple processing cores. In some embodiments, the processor 510 can be a single-threaded processor. In an embodiment, the processor 510 can be a multi-threaded processor.

The user I/O 515 can include a display 516 and/or an input 517, according to an embodiment. It is to be appreciated that the user I/O 515 can be one or more devices connected in communication with the computer device 500 that are physically separate from the computer device 500. For example, the display 516 and input 517 for the desktop computer 502 can be connected in communication but be physically separate from the computer device 500. In some embodiments, the display 516 and input 517 can be physically included with the computer device 500 for the desktop computer 502. In an embodiment, the user I/O 515 can physically be part of the user device 501. For example, the cellular/mobile phone 503, the tablet device 504, and the laptop 505 include the display 516 and input 517 that are part of the computer device 500. The server device 535 generally may not include the user I/O 515. In an embodiment, the server device 535 can be connected to the display 516 and input 517.

The display 516 can include any of a variety of display devices suitable for displaying information to the user. Examples of devices suitable for the display 516 include, but are not limited to, a cathode ray tube (CRT) monitor, a liquid crystal display (LCD) monitor, a light emitting diode (LED) monitor, or the like.

The input 517 can include any of a variety of input devices or input means suitable for receiving an input from the user. Examples of devices suitable for the input 517 include, but are not limited to, a touchscreen, a keyboard, a mouse, a trackball, a button, a voice command, a proximity sensor, an ocular sensing device for determining an input based on eye movements (e.g., scrolling based on an eye movement), or the like. It is to be appreciated that combinations of the foregoing inputs 517 can be included for the user devices 501. In some embodiments the input 517 can be integrated with the display 516 such that both input and output are performed by the display 516.

The memory 520 is generally included to be representative of a random access memory such as, but not limited to, Static Random Access Memory (SRAM), Dynamic Random Access Memory (DRAM), or Flash. In some embodiments, the memory 520 can be a volatile memory. In some embodiments, the memory 520 can be a non-volatile memory. In some embodiments, at least a portion of the memory can be virtual memory.

The storage 530 is generally included to be representative of a non-volatile memory such as, but not limited to, a hard disk drive, a solid state device, removable memory cards, optical storage, flash memory devices, network attached storage (NAS), or connections to storage area network (SAN) devices, or other similar devices that may store non-volatile data. In some embodiments, the storage 530 is a computer readable medium. In some embodiments, the storage 530 can include storage that is external to the computer device 500, such as in a cloud.

The network I/O 525 is configured to transmit data via a network 540. The network 540 may alternatively be referred to as the communications network 540. Examples of the network 540 include, but are not limited to, a local area network (LAN), a wide area network (WAN), the Internet, or the like. In some embodiments, the network I/O 525 can transmit data via the network 540 through a wireless connection using Wi-Fi, Bluetooth, or other similar wireless communication protocols. In some embodiments, the computer device 500 can transmit data via the network 540 through a cellular, 3G, 4G, or other wireless protocol. In some embodiments, the network I/O 525 can transmit data via a wire line, an optical fiber cable, or the like. It is to be appreciated that the network I/O 525 can communicate through the network 540 through suitable combinations of the preceding wired and wireless communication methods.

The server device 535 is generally representative of a computer device 500 that can, for example, respond to requests received via the network 540 to provide, for example, data for rendering an online service (e.g., a website, an app, etc.) on the user devices 501. The server 535 can be representative of a data server, an application server, an Internet server, or the like.

Aspects described herein can be embodied as a system, method, or a computer readable medium. In some embodiments, the aspects described can be implemented in hardware, software (including firmware or the like), or combinations thereof. Some aspects can be implemented in a non-transitory, tangible computer readable medium, including computer readable instructions for execution by a processor. Any combination of one or more computer readable medium(s) can be used.

The computer readable medium can include a computer readable signal medium and/or a computer readable storage medium. A computer readable storage medium can include any tangible medium capable of storing a computer program for use by a programmable processor to perform functions described herein by operating on input data and generating an output. A computer program is a set of instructions that can be used, directly or indirectly, in a computer system to perform a certain function or determine a certain result. Examples of computer readable storage media include, but are not limited to, a floppy disk; a hard disk; a random access memory (RAM); a read-only memory (ROM); a semiconductor memory device such as, but not limited to, an erasable programmable read-only memory (EPROM), an electrically erasable programmable read-only memory (EEPROM), Flash memory, or the like; a portable compact disk read-only memory (CD-ROM); an optical storage device; a magnetic storage device; other similar device; or suitable combinations of the foregoing. A computer readable signal medium can include a propagated data signal having computer readable instructions. Examples of propagated signals include, but are not limited to, an optical propagated signal, an electro-magnetic propagated signal, or the like. A computer readable signal medium can include any computer readable medium that is not a computer readable storage medium that can propagate a computer program for use by a programmable processor to perform functions described herein by operating on input data and generating an output.

An embodiment can be provided to an end-user through a cloud-computing infrastructure. Cloud computing generally includes the provision of scalable computing resources as a service over a network (e.g., the Internet or the like).

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A method for bi-directional integration between an intraoral scanner and one or more dental labs, the method comprising:
a dental product management platform receiving, via a network, an instruction to create a new dental product prescription from an operator via a graphical user interface of the dental product management platform provided on an intraoral computer of the intraoral scanner, wherein the dental product management platform is at a location different from a location of the intraoral scanner;
an application programming interface of the dental product management platform allowing the operator to enter relevant information for the new dental product prescription using the graphical user interface of the dental product management platform provided on the intraoral computer of the intraoral scanner;
a wand of the intraoral scanner scanning a patient's mouth to obtain a scan of the patient, wherein the scan includes scanned image data;
the intraoral computer sending in real time, via the network, the new dental product prescription and the scanned image data obtained from the scan to the dental product management platform;
the dental product management platform receiving the new dental product prescription and the scanned image data from the intraoral computer via the network;
the dental product management platform creating in real time a new dental product order based on the new dental product prescription and the scanned image data, wherein the dental product management platform creating the new dental product order includes the dental product management platform formatting the new dental product prescription into a format designated by an assigned dental lab of the one or more dental labs;
the dental product management platform validating the scanned image data in real time to determine whether the scan is of acceptable quality to fabricate a dental product that meets requirements of the dental product prescription, wherein the dental product management platform validating the scanned image data includes:
an artificial intelligence engine analyzing the scanned image data to review one or more of scan visibility, margin(s), undercut(s), bite visibility, and ditch,
the artificial intelligence engine scoring the scanned image data between 0 and 1 based on the review and categorizing the scanned image data as one of a bad scan, a manageable scan, a good scan, and a perfect scan, and
the artificial intelligence engine comparing a determined score of the scanned image data to a scanned image data threshold level; and upon determining that the scanned image data is below the scanned image data threshold level and thus not of acceptable quality, the dental product management platform provides a notification to the operator via the graphical user interface to use the intraoral scanner to take a second scan of the patient using the intraoral scanner, wherein the graphical user interface displays:

a plurality of rows for a plurality of scanned image data results including a result of the scanned image data as being one of a "Bad" scan, a "Manageable" scan, a "Good" scan, and a "Perfect" scan; and a plurality of columns of information including a dental lab column indicating the assigned dental lab to a particular dental product order, an order identification number column, an upload date column indicating when the scanned image data was uploaded to the dental product management platform, a status column of the scanned image data results, a score column of the scanned image data results, a quality control rating column of the scanned image data results, an additional information column, a PDF link column, and a download link column, wherein the dental lab column and the order identification number column are configured to be empty until one of the one or more dental labs is assigned to the particular dental product order corresponding to the scanned image data results, wherein the status column indicates a status result of each of the scanned image data results, wherein the status result is one of "Good", "Bad", "Manageable", and "Perfect", wherein the score column indicates a score result of each of the plurality of scanned image data results between 0 to 1, wherein the quality control rating column indicates a category result of each of the plurality of scanned image data results including one of "Bad", "Manageable", "Good", and "Perfect", wherein the additional information column is configured to include reasons for a particular status, score or quality control rating to assist the operator when taking the second scan, wherein the PDF link column provides information of a particular scanned image data result in a PDF file, and wherein the download link column is configured to allow the operator to download the information of the particular scanned image data result.

2. The method of claim 1, wherein the artificial intelligence engine determines that the scanned image data is of acceptable quality when the score of the scanned image data is at or above the scanned image data threshold level.

3. The method of claim 1, wherein the artificial intelligence engine determines that the scanned image data is not of acceptable quality when the score of the scanned image data is below the scanned image data threshold level.

4. The method of claim 1, further comprising upon determining that the scanned image data is of acceptable quality, the dental product management platform:

allocating the new dental product order to the assigned dental lab, and sending the new dental product order that includes the new dental product prescription and the scanned image data to the assigned dental lab.

5. A dental product management system configured to provide bi-directional integration between one or more intraoral scanners and one or more dental labs, the dental product management system comprising:

a particular intraoral scanner of the one or more intraoral scanners, wherein the particular intraoral scanner includes:

a wand configured to scan a patient's mouth to obtain a scan of the patient, wherein the scan includes scanned image data, and an intraoral computer configured to access a graphical user interface of a dental product management platform and send in real time, via a network, a new dental product prescription and the scanned image data obtained from the scan to the dental product management platform; and the dental product management platform that includes the graphical user interface accessible by the particular intraoral scanner, wherein the dental product management platform is at a location different from a location of the intraoral scanner, wherein the dental product management platform includes an application programming interface configured to allow an operator to enter relevant information for the new dental product prescription using the graphical user interface of the dental product management platform provided on the intraoral computer of the intraoral scanner, wherein the dental product management platform is configured to:

receive an instruction to create the new dental product prescription from the operator via the graphical user interface of the dental product management platform provided on the intraoral computer;

receive the new dental product prescription and the scanned image data from the intraoral computer via the network;

create in real time a new dental product order based on the new dental product prescription and the scanned image data which includes the dental product management platform formatting the new dental product prescription into a format designated by an assigned dental lab of the one or more dental labs;

validate, using an artificial intelligence engine, the scanned image data in real time to determine whether the scan is of acceptable quality to fabricate a dental product that meets requirements of the new dental product prescription, wherein the artificial intelligence engine is configured to:

analyze the scanned image data to review one or more of scan visibility, margin(s), undercut(s), bite visibility, and ditch, score the scanned image data between 0 and 1 based on the review and categorizing the scanned image data as one of a bad scan, a manageable scan, a good scan, and a perfect scan, and compare a determined score of the scanned image data to a scanned image data threshold level; and upon determining that the scanned image data is below the scanned image data threshold level and thus not of acceptable quality:

provide a notification to the operator via the graphical user interface to use the particular intraoral scanner to take a second scan of the patient using the particular intraoral scanner, wherein the graphical user interface displays:

a plurality of rows for a plurality of scanned image data results including a result of the scanned image data as being one of a "Bad" scan, a "Manageable" scan, a "Good" scan, and a "Perfect" scan; and a plurality of columns of information including a dental lab column indicating the assigned dental lab to a particular dental product order, an order identification number column, an upload date column indicating when the scanned image data was uploaded to the dental product management platform, a status column of the scanned image data results, a score column of the scanned image data results, a quality control rating column of the scanned image data results, an additional information column, a PDF link column, and a download link column, wherein the dental lab column and the order identification number column are configured to be empty until one of the one or more dental labs is assigned to the particular dental product order corresponding to the scanned image data results, wherein the status column indicates a status result of each of the scanned image data results, wherein the status result is one of "Good", "Bad", "Manageable", and "Perfect", wherein the score column indicates a score result of each of the plurality of scanned image data results between 0 to 1, wherein the quality control rating column indicates a category result of each of the plurality of scanned image data results including one of "Bad", "Manageable", "Good", and "Perfect", wherein the additional information column is configured to include reasons for a particular status, score or quality control rating to assist the operator when taking the second scan, wherein the PDF link column provides information of a particular scanned image data result in a PDF file, and wherein the download link column is configured to allow the operator to download the information of the particular scanned image data result.

6. The dental product management system of claim 5, wherein the artificial intelligence engine is configured to determine that the scanned image data is of acceptable quality when the score of the scanned image data is at or above the scanned image data threshold level.

7. The dental product management system of claim 5, wherein the artificial intelligence engine is configured to determine that the scanned image data is not of acceptable quality when the score of the scanned image data is below the scanned image data threshold level.

8. The dental product management system of claim 5, wherein the dental product management platform is configured to:

upon determining that the scanned image data is of acceptable quality:

allocate the new dental product order to the assigned dental lab, and send the new dental product order that includes the new dental product prescription and the scanned image data to the assigned dental lab.

* * * * *